United States Patent
Mueller

(10) Patent No.: US 12,078,650 B2
(45) Date of Patent: Sep. 3, 2024

(54) METHOD FOR UNSEALING AN OPENING OF A LABORATORY SAMPLE CONTAINER, METHOD FOR HANDLING A LABORATORY SAMPLE CONTAINER, LABORATORY APPARATUS AND LABORATORY AUTOMATION SYSTEM

(71) Applicant: Roche Diagnostics Operations, Inc., Indianapolis, IN (US)

(72) Inventor: Daniel Mueller, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 331 days.

(21) Appl. No.: 16/295,179

(22) Filed: Mar. 7, 2019

(65) Prior Publication Data

US 2019/0293670 A1   Sep. 26, 2019

(30) Foreign Application Priority Data

Mar. 26, 2018 (EP) ..................................... 18164036

(51) Int. Cl.
*G01N 35/04* (2006.01)
*G01N 35/10* (2006.01)
(Continued)

(52) U.S. Cl.
CPC ............. *G01N 35/04* (2013.01); *G01N 35/10* (2013.01); *B01D 35/02* (2013.01); *B01F 25/00* (2022.01);
(Continued)

(58) Field of Classification Search
CPC ...... G01N 35/04; G01N 35/10; G01N 33/543; G01N 33/558; G01N 1/28; G01N 35/00;
(Continued)

(56) References Cited

U.S. PATENT DOCUMENTS

| 4,925,684 A | 5/1990 | Simon |
| 8,528,194 B2 | 9/2013 | Pedrazzini |

(Continued)

FOREIGN PATENT DOCUMENTS

| EP | 1944345 A1 | 7/2008 |
| EP | 2995958 A1 | 3/2016 |

(Continued)

OTHER PUBLICATIONS

Wang, "The Effect of Peeling Rate and Peeling Angle on the Peeling Strength", May 2014, A Thesis Presented to The Graduated Faculty of The University of Akron, pp. 1-44. (Year: 2014).*
(Continued)

*Primary Examiner* — P. Kathryn Wright
*Assistant Examiner* — Curtis A Thompson
(74) *Attorney, Agent, or Firm* — Thomas E. Lees, LLC

(57) ABSTRACT

A method for unsealing an opening of a laboratory sample container containing a sample is presented. The opening is sealed by a closure attached to the laboratory sample container by an adhesive. An adhesive strength of the adhesive is lowerable by treatment. The method comprises treating the adhesive such that its adhesive strength is lowered and removing the closure from the laboratory sample container.

8 Claims, 2 Drawing Sheets

(51) Int. Cl.
  *B01D 35/02* (2006.01)
  *B01F 25/00* (2022.01)
  *B01L 3/00* (2006.01)
  *B01L 3/02* (2006.01)
  *B04B 5/04* (2006.01)
  *B04B 11/04* (2006.01)
  *B23P 19/00* (2006.01)
  *B65B 7/16* (2006.01)
  *B65B 7/28* (2006.01)
  *G01N 1/28* (2006.01)
  *G01N 21/77* (2006.01)
  *G01N 33/543* (2006.01)
  *G01N 35/00* (2006.01)
  *G01N 35/02* (2006.01)

(52) U.S. Cl.
  CPC . *B01L 3/00* (2013.01); *B01L 3/02* (2013.01); *B04B 5/04* (2013.01); *B04B 11/04* (2013.01); *B23P 19/00* (2013.01); *B65B 7/16* (2013.01); *B65B 7/28* (2013.01); *G01N 1/28* (2013.01); *G01N 21/77* (2013.01); *G01N 33/543* (2013.01); *G01N 35/00* (2013.01); *G01N 2035/00346* (2013.01); *G01N 35/02* (2013.01); *G01N 2035/0405* (2013.01)

(58) Field of Classification Search
  CPC .................. G01N 21/77; G01N 35/02; G01N 2035/00346; G01N 2035/0405; B23P 19/00; B01D 35/02; B01F 5/00; B04B 5/04; B04B 11/04; B01L 3/02; B01L 3/00; B65B 7/28; B65B 7/16; B65B 69/0066
  See application file for complete search history.

(56) References Cited

U.S. PATENT DOCUMENTS

| | | | |
|---|---|---|---|
| 2002/0041828 A1 | 4/2002 | Spitz et al. | |
| 2003/0040011 A1* | 2/2003 | Barth | G01N 35/028 435/7.1 |
| 2003/0064592 A1* | 4/2003 | Yamamoto | H01L 21/67132 438/689 |
| 2004/0007327 A1* | 1/2004 | Kobayashi | H01L 21/6836 156/353 |
| 2005/0145328 A1* | 7/2005 | Lim | B29C 45/14754 156/272.2 |
| 2006/0056945 A1 | 3/2006 | Daio | |
| 2007/0074822 A1* | 4/2007 | Akechi | H01L 21/6835 156/941 |
| 2007/0099550 A1* | 5/2007 | Ko | B24B 37/345 451/41 |
| 2007/0134131 A1 | 6/2007 | Watson et al. | |
| 2007/0248496 A1* | 10/2007 | Bondioli | B65B 7/2878 422/400 |
| 2010/0011555 A1* | 1/2010 | Pedrazzini | B67B 7/00 29/426.5 |
| 2014/0020174 A1* | 1/2014 | Evans | E03F 5/0407 4/679 |
| 2014/0093972 A1 | 4/2014 | Bernay et al. | |
| 2014/0210995 A1* | 7/2014 | Abe | H01L 33/005 348/93 |
| 2016/0229565 A1* | 8/2016 | Margner | G01N 35/04 |
| 2017/0205317 A1* | 7/2017 | Zhang | G01N 1/31 |

FOREIGN PATENT DOCUMENTS

| | | |
|---|---|---|
| JP | H04-350893 A | 12/1992 |
| JP | 2508303 Y2 | 5/1996 |
| JP | 2941464 B2 | 8/1999 |
| JP | 2008-018960 A | 1/2008 |
| JP | 2010-99061 A | 5/2010 |
| JP | 2011-121618 A | 6/2011 |
| JP | 2013108797 A * | 6/2013 |
| JP | 2013-141651 A | 7/2013 |
| JP | 2014-206462 A | 10/2014 |
| JP | 2015-078886 A | 4/2015 |
| JP | 2017-26381 A | 2/2017 |
| JP | 2017026381 A * | 2/2017 |
| JP | 2017-150844 A | 8/2017 |
| WO | 2000/069389 A2 | 11/2000 |
| WO | 2003/062508 A1 | 7/2003 |
| WO | 2005/026742 A1 | 3/2005 |
| WO | 2010/027283 A1 | 3/2010 |
| WO | 2013/113874 A1 | 8/2013 |
| WO | 2016/018910 A1 | 2/2016 |

OTHER PUBLICATIONS

IHS GlobalSpec, "UV Curing Adhesives Information", https://web.archive.org/web/20140812115452/https://www.globalspec.com/learnmore/materials_chemicals/adhesives/uv_curing_adhesives_radiation_light_curable, Aug. 12, 2014 (Year: 2014).*
European Search Report issued Sep. 27, 2018, in Application No. 18164036, 2 pp.

* cited by examiner

METHOD FOR UNSEALING AN OPENING OF A LABORATORY SAMPLE CONTAINER, METHOD FOR HANDLING A LABORATORY SAMPLE CONTAINER, LABORATORY APPARATUS AND LABORATORY AUTOMATION SYSTEM

CROSS-REFERENCE TO RELATED APPLICATIONS

This application claims priority to EP 18164036.8, filed Mar. 26, 2018, which is hereby incorporated by reference.

BACKGROUND

The present disclosure generally relates to a method for unsealing an opening of a laboratory sample container, a method for handling a laboratory sample container comprising such a method, a laboratory apparatus for unsealing an opening of a laboratory sample container and a laboratory automation system comprising such a laboratory apparatus.

In laboratories, some types of laboratory stations or instruments and/or analysis may require laboratory sample containers such as sample tubes to be open for processing such as, for example, pretreating and/or analyzing, samples contained by the laboratory sample containers.

Therefore, there is a need for a method for unsealing an opening of a laboratory sample container in an improved manner.

SUMMARY

According to the present disclosure, a method for unsealing an opening of a laboratory sample container containing a sample is disclosed. The opening can be sealed by a closure attached to the laboratory sample container by an adhesive. An adhesive strength of the adhesive can be lowerable by treatment. The method can comprise treating the adhesive such that its adhesive strength is lowered and removing the closure from the laboratory sample container Accordingly, it is a feature of the embodiments of the present disclosure to provide for a method for unsealing an opening of a laboratory sample container in an improved manner. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
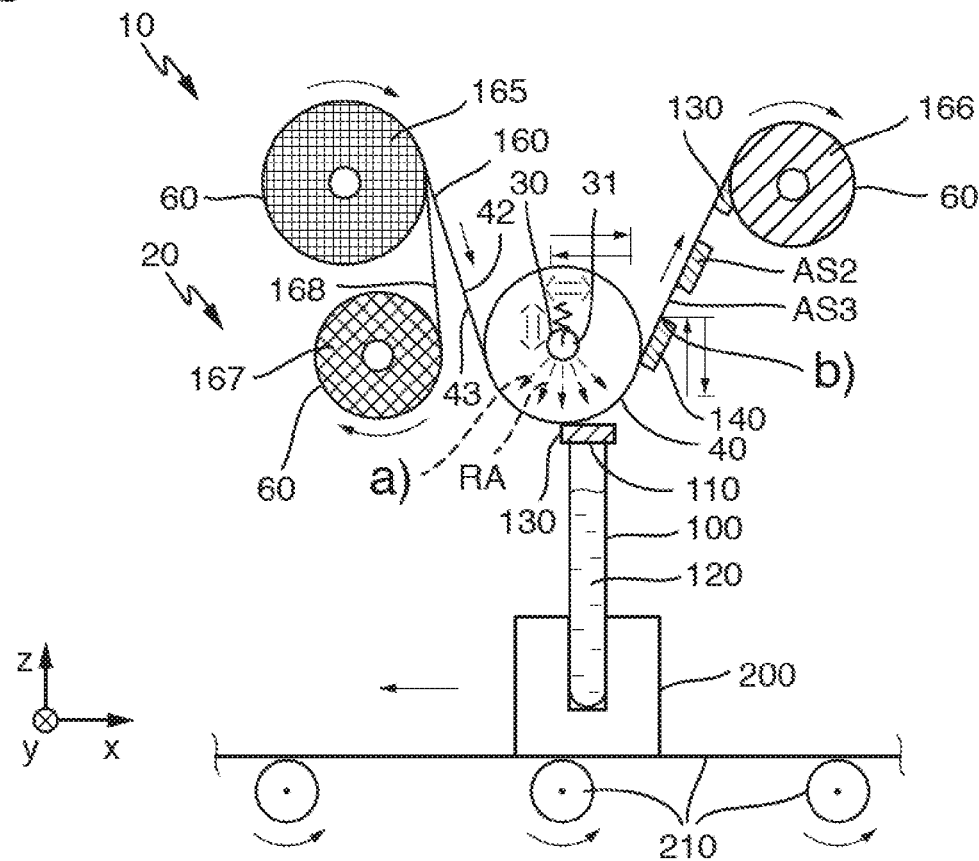
FIG. 1 illustrates a method for handling a laboratory sample container comprising a method for unsealing an opening of the laboratory sample container and a laboratory automation system for handling the laboratory sample container comprising a laboratory apparatus for unsealing the opening of the laboratory sample container according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for unsealing such as, for example, automatically unsealing, or opening an opening or a mouth of a laboratory sample container containing or comprising a sample is presented. The opening can be sealed or closed by a closure attached or adhered to the laboratory sample container by an adhesive. An adhesive strength, or a peel adhesion, of the adhesive can be lowerable or reducible or decreasable such as, for example, from a first value to a second value, by treatment such as, for example, external and/or physical treatment. The method can comprise the steps: a) treating such as, for example, automatically treating, the adhesive such that its adhesive strength is lowered such as, for example, from the first value to the second value and b) removing such as, for example, automatically removing, the closure from the laboratory sample container.

The method can enable the unsealing of the opening of the laboratory sample container in a soft, or gentle, manner or way in comparison to unsealing the opening of the laboratory sample container without treating the adhesive, i.e., without lowering the adhesive strength, but by only removing such as, for example, pulling off, the closure from the laboratory sample container.

In one embodiment, the method may enable the reduction or avoidance of a negative impact on the sample integrity. The method may enable the reduction or prevention of introducing a vibration or a shock to the laboratory sample container. Thereby, the method may enable the reduction or prevention of a spilling of the sample such as, for example, out of the laboratory sample container. Thereby, contamination or cross-contamination of the laboratory sample container and/or the sample and/or other laboratory sample containers and/or other samples and/or a laboratory apparatus and/or a laboratory automation system may be reduced or avoided.

Furthermore, the treating method may enable that less or no adhesive residues are left, for example, on or at the laboratory sample container after the unsealing. Thereby, a sealing such as, for example, a re-sealing, of the same opening of the same laboratory sample container may be facilitated such as, for example, repeated opening-closing-cycles may be allowed.

Moreover, the removing method may enable that less or no damage may be introduced to the laboratory sample container. Thereby, a sealing such as, for example, a re-sealing, of the same opening of the same laboratory sample container may be facilitated such that repeated opening-closing-cycles may be allowed.

Further, the method may enable that no complex mechanics may be necessary for unsealing.

Furthermore, the method may enable a fast unsealing such as, for example, of about 5 seconds or less per laboratory sample container.

In one embodiment, method step b) may be performed simultaneously with method step a) and/or after method step a). In one embodiment, the closure may be left on or at the laboratory sample container or its opening during or even until after the treating of the adhesive or the lowering of its adhesive strength. Treating the adhesive or lowering the adhesive strength, respectively, may be denoted as releasing the closure. In one embodiment, then the closure may be easily removed from the laboratory sample container since the adhesive strength can be lowered or the closure can be released, respectively. Removing from the laboratory sample container may be denoted as taking up or off or peeling off from the laboratory sample container. Unsealing may be denoted as desealing. Additionally, or alternatively, the treating may be different from the removing.

The sample may be a blood sample, a serum sample, a plasma sample, a urine sample, a CFS sample, a body sample, a water sample, a chemical sample, a quality control (QC) material or a calibrator and the like. In one embodiment, the sample may be a liquid.

The laboratory sample container may be designed as a tube and may have the opening at an upper, top, and/or face end. In one embodiment, the laboratory sample container may be configured to contain only one sample. Alternatively, or additionally, the laboratory sample container may be designed as a multi-well-plate and may have the opening at an upper end. In one embodiment, the laboratory sample container may be configured to contain a plurality of samples such as, for example, separated samples. Furthermore, the laboratory sample container may be made of glass or transparent and/or translucent and/or opaque plastic such as, for example, polypropylene (PP) and/or polystyrene (PS) and/or polyethylene terephthalate (PET), or any other such as, for example, somewhat, solid material. The opening may be defined by an end of a wall and/or a circumference of the laboratory sample container.

The closure may comprise rubber and/or plastic and/or metal or may completely consist of rubber and/or plastic and/or metal. In one embodiment, a closure material may be polyvinyl chloride (PVC), polyolefin (PO), polyethylene terephthalate (PET) and/or aluminum. In one embodiment, the closure may comprise a sample-repellent property such as, for example, a liquid-tight property. The closure may enable protection against evaporation, contamination and/or reaction of the sample and/or any other impact that might influence the sample such as, for example, influence pretreating and/or analyzing. Additionally, or alternatively, the closure may be embodied as a foil such as, for example, a flexible foil, or film or tape or as a lid such as, for example, a rigid lid, or a plug. A thickness of the closure may be in the micrometer (µm) range such as, in one embodiment, in a range from about 20 µm to about 400 µm, in another embodiment, in a range from about 50 µm to about 300 µm, in still another embodiment, in a range from about 100 µm to about 230 µm, and in still yet another embodiment about 100 µm.

The closure such as, for example, a surface of the closure, may be provided with the adhesive.

The second value such as, for example, after the treatment or treating may be lower than the first value such as, for example, before the treatment or treating. In one embodiment, the adhesive may have a high enough adhesive strength or a high enough peel adhesion before the treating such as, for example, for sealing or closing of the opening of the laboratory sample container, but which may be significantly reduced upon treating. In one embodiment, the adhesive strength of its first value before the treating may be in a range from about 1000 Millinewton (mN) per 25 Millimeter (mm) to at least about 50000 mN/25 mm, in another embodiment, in a range from about 10000 mN/25 mm to about 30000 mN/25 mm, and in still another embodiment, in a range from about 15000 mN/25 mm to about 25000 mN/25 mm. The lowered adhesive strength of its second value after the treating may be in a range from about 0 mN/25 mm to about 1000 mN/25 mm, in another embodiment in a range from about 50 mN/25 mm to about 800 mN/25 mm, and in yet another embodiment, in a range from about 100 mN/25 mm to about 600 mN/25 mm. In one embodiment, the adhesive strength or its value may be measured on stainless steel as an adherent with a removing or peeling angle of about 180 degrees (°) and a removing or peeling speed of about 300 mm/minute. Additionally, or alternatively, a thickness of the adhesive may be in the micrometer (µm) range such as, for example, in one embodiment, in a range from about 10 µm to about 300 µm, in another embodiment in a range from about 30 µm to about 200 µm, in yet another embodiment in a range from about 75 µm to about 130 µm, and in still yet another embodiment about 130 µm. The adhesive may be denoted as glue.

In one embodiment, a thickness of the closure plus the adhesive may be in a range from about 30 µm to about 700 µm, in another embodiment in a range from about 80 µm to about 500 µm, in yet another embodiment in a range from about 175 µm to about 360 µm, and still yet another embodiment about 230 µm.

According to an embodiment, the adhesive strength can be lowerable by radiation treatment such as, for example, by ultraviolet (UV) radiation and/or by heat treatment such as, for example, by heat with a temperature with a minimum of about 50 degrees Celsius (° C.), or in another embodiment with a minimum of about 120° C., and with a maximum of about 200° C. Step a) of the method can comprise treating the adhesive by radiation such as, for example, by UV radiation, and/or by heat such as, for example, by heat with a temperature with a minimum of about 50° C., in another embodiment with a minimum of about 120° C., and with a maximum of about 200° C. In one embodiment, this may be no normal conditions for the sample or the laboratory sample container. Thereby, the adhesive may not be inadvertently treated. In one embodiment, the UV radiation may be UV-A radiation such as, for example, having a wavelength from about 380 to about 315 Nanometer (nm) and in another embodiment of about 365 nm. The UV-A radiation may have little or no negative impact on the Deoxyribonucleic acid (DNA), if present, in the sample. The UV radiation may have an intensity of about 100 Milliwatt (mW) per square centimeter ($cm^2$) and in another embodiment of about 1000 $mW/cm^2$. The UV radiation may have a dosage from about 100 Millijoule (mJ) per $cm^2$ to about 700 $mJ/cm^2$ or in another embodiment of about 500 $mJ/cm^2$. Additionally, or alternatively, the radiation may be laser radiation. In one embodiment, the heat treatment may be performed for a maximum of about 60 seconds (s), in another embodiment for a maximum of about 30 s, in still another embodiment for a maximum of about 10 s, in yet another embodiment for a maximum of about 5 s, and for a minimum of about 1 s. Thereby, a negative impact on the sample by the heat treatment may be reduced or avoided. In one embodiment, the laboratory sample container may comprise a low heat conductivity. Thereby, a heat or thermal transfer from the opening of the laboratory sample container to the contained sample, which typically does not have to completely fill the laboratory sample container to its opening, may be reduced or avoided. This may be denoted as local treatment. The adhesive may be denoted radiation-sensitive and/or heat-sensitive adhesive.

According to an embodiment, method step a) can comprise exposing such as, for example, automatically exposing, the radiation to the adhesive and/or the opening and/or a rim of the laboratory sample container along a direction different from such as, for example, substantially perpendicular to, a line between the adhesive and the sample. Additionally, or alternatively, method step a) can comprise focusing such as, for example, automatically focusing, the radiation on the adhesive or the opening or the rim such as, for example, by an automatically influence able phase plate. Thereby, a negative impact on the sample which typically does not have to completely fill the laboratory sample container to its opening by the radiation treatment can be reduced or avoided. This may be denoted as local treatment. In one embodiment, the radiation may be exposed under an angle or from below.

According to an embodiment, the adhesive can comprise a reactive site to UV radiation. In one embodiment, the adhesive may be denoted as UV curable. Additionally, or alternatively, the adhesive may comprise an acrylic copolymer, a photopolymerization initiator, a curing agent and a UV curable oligomer such as, for example, with a backbone formed out of polyester, epoxy or urethane and with a functional group such as, for example, diacrylourethane and/or UV curable polyfunctional monomers. In one embodiment, such an adhesive material may crosslink by the UV radiation treating. Thereby, the adhesive strength may be lowered such as, for example, by the generation of microvoids in between the adhesive and the laboratory sample container suggested by volume contraction as a possible mechanism. Additionally, or alternatively, the adhesive can comprise a foaming agent such as, for example, heat-expandable microspheres. In one embodiment, such an adhesive material may foam, or expand, by the heat treating. Thereby, the adhesive strength may be lowered such as, for example, by reducing an adhesion area such as, for example, its value, in between the adhesive and the laboratory sample container.

According to an embodiment, method step b) can comprise sucking such as, for example, automatically sucking, the closure from the laboratory sample container by vacuum. Additionally, or alternatively, method step b) can comprise attaching such as, for example, automatically attaching, a take-up to the closure by another adhesive. Another adhesive strength such as, for example, its value, of the another adhesive can be such that another adhesive force such as, for example, its value, between the take-up and the attached closure can be higher than an adhesive force such as, for example, its value, between the closure and the laboratory sample container by the lowered adhesive strength of the treated adhesive. Removing such as, for example, automatically removing, the take-up with the attached closure from the laboratory sample container. Thereby, the force required to remove or to peel off the take-up from the closure can be higher than the force required to remove or to peel off the closure from the laboratory sample container such as, for example, after the adhesive strength is lowered. In one embodiment, the required force such as, for example, its value, may depend on the another adhesive strength of the another adhesive and/or on the lowered adhesive strength of the treated adhesive and/or on an adhesion area such as, for example, its value, in between the take-up and the closure and/or on an adhesion area such as, for example, its value, in between the closure and the laboratory sample container and/or on a material property and/or a geometry of the closure and/or on a material property and/or a geometry of the laboratory sample container. Additionally, or alternatively, the another adhesive may be of the same adhesive type as the adhesive or another adhesive. Additionally, or alternatively, the take-up such as, for example, a surface of the take-up, may be provided with the another adhesive.

Additionally, or alternatively, method step b) may comprise removing the closure from the laboratory sample container by a mechanical device such as, for example, a mechanical gripper and/or a blade.

According to an embodiment, the method may comprise the step of pre-treating the laboratory sample container such as, for example, its opening such as, for example, after removing the closure and/or before sealing the opening of the laboratory sample container such as, for example, by attaching a closure to the laboratory sample container such as, for example, by an adhesive. Thereby, an adhesion such as, for example, an adhesion strength or force value, of the such as, for example, attached, closure on or to the laboratory sample container may be improved such as, for example, increased such as, for example, in the case where the laboratory sample container comprise or consist of a low-energy material such as, for example, polypropylene (PP). Thereby, a risk, that the seal may be not tight such as, for example, liquid-untight may be reduced or avoided.

A method for handling such as, for example, for automatically handling, a laboratory sample container containing a sample is also presented. The method can comprise the steps of sealing such as, for example, automatically sealing, or closing an opening of the laboratory sample container by attaching or adhering a closure to the laboratory sample container by an adhesive. An adhesive strength of the adhesive can be lowerable such as, for example, from a first value to a second value, by treatment. Unsealing such as, for example, automatically unsealing, the opening by a method as described above such as, for example, after the sealing.

The sealing can enable storage or archiving and cooling the sample contained by the laboratory sample container. In one embodiment, the sample may be stored or archived at a maximum temperature of about 5° C., and, in one embodiment, at minimum temperature of minus 80° C. and, in another embodiment, at minimum of minus 30° C. Additionally, or alternatively, the sealing may enable the movement or shipment of the sample contained by the laboratory sample container. Further, additionally, or alternatively, the method may enable a fast sealing.

The sample, the laboratory sample container, the closure and/or the adhesive may be embodied as described above.

Additionally, or alternatively, for example, before sealing, the laboratory sample container such as, for example, its opening, may be pre-treated as described above.

According to an embodiment, the adhesive can be pressure-sensitive. The sealing can comprise pressing such as, for example, automatically pressing, the closure against the laboratory sample container such as, for example, with the adhesive in between the closure and the laboratory sample container.

According to an embodiment, the method can comprise supplying such as, for example, automatically supplying, the closure by a roller tape. Moving such as, for example, automatically moving, the roller tape with the closure to the opening of the laboratory sample container for the sealing. In one embodiment, the closure may be pre-cut or partially pre-cut and available from the roller tape.

According to an embodiment, the sealing can comprise attaching such as, for example, automatically attaching, a closure blank such as, for example, the roller tape, if present, to the laboratory sample container. Cutting-out such as, for example, automatically cutting-out, the closure out of the attached closure blank such as, for example, the roller tape, if present. In one embodiment, the closure blank may be supplied by a roller tape as described above. Additionally, or alternatively, the closure blank such as, for example, the roller tape, may be partially pre-cut or perforated, respectively. Additionally, or alternatively, the closure blank such as, for example, a surface of the closure blank, may be provided with the adhesive. The cutting-out may comprise punching or laser cutting.

A laboratory apparatus or device for unsealing an opening of a laboratory sample container containing a sample is also presented. The opening can be sealed by a closure attached to the laboratory sample container by an adhesive. An adhesive strength of the adhesive can be lowerable by treatment. The laboratory apparatus can comprise a treater and a remover. The treater can be configured to treat the adhesive such that its adhesive strength can be lowered. The remover can be configured to remove the closure from the laboratory sample container.

In one embodiment, the laboratory apparatus may be configured to perform a method such as, for example, for unsealing the opening of the laboratory sample container, as described above. By use of the method, the advantages of the method, as discussed above, may be made applicable for the laboratory apparatus.

Furthermore, the laboratory apparatus may enable that no complex mechanics may be needed for unsealing. Thereby, a maintenance effort of the laboratory apparatus may be lowered.

Moreover, the laboratory apparatus may enable a fast unsealing. Thereby, the laboratory apparatus may enable a high throughput such as, for example, of up to 1200 samples or containers per hour.

Further, the laboratory apparatus may have a compact design such as, for example, a small foot-print.

Furthermore, the laboratory apparatus or its treater or its remover may be compatible with a small space or pitch between laboratory sample containers on a rack.

The laboratory apparatus may be denoted as unsealer.

Additionally, or alternatively, the treater may be different from the remover.

According to an embodiment, the adhesive strength can be lowered by radiation treatment such as, for example, by UV radiation, and/or by heat treatment such as, for example, by heat with a temperature of a minimum of about 50° C. or in another embodiment, of a minimum of about 120° C., and with a maximum temperature of about 200° C. The treater can be configured to treat the adhesive by radiation such as, for example, by UV radiation, and/or by heat such as, for example, by heat with a temperature of minimum of about 50° C. or in another embodiment, a minimum of about 120° C., and with a maximum of about 200° C. The treater may be denoted as radiation treater such as, for example, UV radiation treater. In one embodiment, the treater may comprise a radiation source such as, for example, a UV radiation source. Additionally, or alternatively, the treater may comprise an optic such as, for example, for exposing the radiation to the adhesive along a direction different from a line between the adhesive and the sample and/or for focusing the radiation on the adhesive. Additionally, or alternatively, the treater may be denoted as heat treater. In one embodiment, the treater may comprise a heat source.

According to an embodiment, the remover can comprise a sucker. The sucker can be configured to suck the closure from the laboratory sample container by vacuum. Additionally, or alternatively, the remover can be configured to attach a take-up to the closure by another adhesive. The another adhesive strength of the another adhesive can be such that an adhesive force between the take-up and the attached closure can be higher than an adhesive force between the closure and the laboratory sample container by the lowered adhesive strength of the treated adhesive. Furthermore, the remover can be configured to remove the take-up with the attached closure from the laboratory sample container. In one embodiment, the sucker may be denoted as vacuum sucker. The sucker may comprise a vacuum chuck and/or a vacuum source.

Additionally, or alternatively, the remover may comprise a mechanical device such as, for example, a mechanical gripper and/or a blade, for removing the closure from the laboratory sample container.

According to an embodiment, the remover can comprise at least one roller receptacle and mover. The roller receptacle and mover can be configured to supply the take-up by a roller tape such as, for example, of a take-up-roll. Furthermore, the roller receptacle and mover can be configured to move the roller tape with the take-up with the attached closure from the laboratory sample container.

According to an embodiment, the laboratory apparatus may comprise a pre-treater. The pre-treater may be configured to pre-treat the laboratory sample container such as, for example, its opening such as, for example, after removing the closure and/or before sealing the opening of the laboratory sample container such as, for example, by attaching a closure to the laboratory sample container such as, for example, by an adhesive.

A laboratory automation system for handling a laboratory sample container containing a sample is also presented. The laboratory automation system can comprise a sealer and a laboratory apparatus as described above. The sealer can be configurable to seal an opening of the laboratory sample container by attaching a closure to the laboratory sample container by an adhesive. An adhesive strength of the adhesive can be lowerable by treatment.

In one embodiment, the laboratory automation system or its sealer, respectively, may be configured to perform the method such as, for example, for handling the laboratory sample container such as, for example, for sealing the opening of the laboratory sample container, as described above. By use of the method, the advantages of the method, as discussed above, may be made applicable for the laboratory automation system.

Furthermore, by use of the laboratory apparatus, the advantages of the laboratory apparatus, as discussed above, may be made applicable for the laboratory automation system.

Moreover, the laboratory automation system or its sealer may enable a fast sealing. Thereby, the laboratory automation system or its sealer may enable a high throughput such as, for example, of up to 1500 samples or containers per hour.

Further, the laboratory automation system or its sealer may have a compact design such as, for example, a small foot-print.

Furthermore, the laboratory automation system or its sealer may be compatible with a small space or pitch between laboratory sample containers on a rack.

Moreover, the sealer may be configured to press the closure against the laboratory sample container. In one embodiment, the sealer may comprise a pressure pad.

Additionally, or alternatively, the laboratory automation system may comprise a pre-treater. The pre-treater may be configured to pre-treat the laboratory sample container such as, for example, its opening such as, for example, before sealing the laboratory sample container its opening.

According to an embodiment, the sealer can comprise at least one roller receptacle and mover which may be different from the at least one roller receptacle and mover, if present, of the remover. The roller receptacle and mover can be configured to supply the closure by a roller tape such as, for example, of a closure-supply-roll or a closure-blank-supply-roll. Furthermore, the roller receptacle and mover can be configured to move the roller tape with the closure to the opening of the laboratory sample container for the sealing. In one embodiment, the sealer may be configured to attach a closure blank such as, for example, the roller tape, to the laboratory sample container. Furthermore, the sealer may be configured to cut-out the closure out of the attached closure blank such as, for example, the roller tape. The sealer may comprise an attacher and a cutter. In one embodiment, the cutter may comprise a cutting or pinch blade and/or a laser.

The laboratory apparatus or its treater and/or its remover and/or the laboratory automation system or its sealer may be denoted as a laboratory station(s). The laboratory automation system may comprise a number of laboratory stations. The number of laboratory stations may comprise pre-analytical, analytical and/or post-analytical laboratory stations. Pre-analytical laboratory stations may be configured to perform any kind of pre-processing of samples and/or laboratory sample containers. Analytical laboratory stations may be configured to use a sample or part of the sample and a reagent to generate a measurement signal, the measurement signal indicating if and in which concentration, if any, an analyte exists. Post-analytical laboratory stations may be configured to perform any kind of post-processing of samples and/or laboratory sample containers. The pre-analytical, analytical and/or post-analytical laboratory stations may comprise at least one of an aliquot station, a centrifugation station, an archiving station, a pipetting station, a sorting station, a tube type identification station, a sample quality determining station, an add-on buffer station, a liquid level detection station, a decapping/recapping station, a pushing station, a belt station, a conveying system station and/or a gripper station.

Additionally, the laboratory apparatus and/or the laboratory automation system may comprise a control device for controlling the laboratory apparatus and/or the laboratory automation system. The control device may comprise or be an integrated circuit, a tablet computer, a smartphone or a computer.

The step of pre-treating and/or the pre-treater may be independent of the unsealing, the sealing, the laboratory apparatus, the laboratory automation system, the sealer and/or the adhesive such as, for example, which adhesive strength is lowerable by treatment, an independent subject matter. In other words, a method may comprise the step of pre-treating a laboratory sample container such as, for example, its opening, in order to enhance an attaching force of a closure of the sample container to the sample container. According to an embodiment of this method, the method may further comprise the step of sealing the pre-treated opening of the pre-treated laboratory sample container by attaching a closure to the laboratory sample container such as, for example, by an adhesive such as, for example, which adhesive strength may be lowerable by treatment. In other words, a pre-treater may be configured to pre-treat a laboratory sample container such as, for example, its opening. Furthermore, a laboratory automation system may comprise the pre-treater and a sealer, wherein the sealer may be configured to seal the pre-treated opening of the pre-treated laboratory sample container by attaching a closure to the laboratory sample container such as, for example, by an adhesive such as, for example, in which the adhesive strength may be lowerable by treatment.

Thereby, an adhesion such as, for example, an adhesion strength or force value, of the attached closure on or to the laboratory sample container may be improved such as, for example, increased such as, for example, in the case where the laboratory sample container comprises or consists of a low-energy material such as, for example, polypropylene (PP). Thereby, a risk, that the seal may be not tight such as, for example, liquid-untight may be reduced or avoided.

In one embodiment, pre-treating may comprise increasing a surface free energy such as, for example, its value, of the laboratory sample container such as, for example, of a rim of the opening. In one embodiment, the pre-treating may comprise pre-treating by UV radiation such as, for example, by UV C radiation, by flame, by corona, by plasma and/or by acid etching and/or by the use of a solvent based adhesion promoter. In other words, a surface of the laboratory sample container or its rim, respectively, may be functionalized such as, for example, by oxygen such as, for example, by ozone.

Additionally, or alternatively, pre-treating may comprise increasing an adhesion area such as, for example, its value, of the laboratory sample container such as, for example, of the rim of the opening. In one embodiment, the pre-treating may comprise melting and/or roughening the laboratory sample container or its rim.

Additionally, or alternatively, pre-treating may comprise cleaning the laboratory sample container such as, for example, the rim of the opening such as, for example, from adhesive residues and/or liquids and/or coatings such as, for example, anticoagulants.

FIGS. 1 to 4 show a method for handling a laboratory sample container 100 containing a sample 120. The method can comprise a method for unsealing an opening 110 of the laboratory sample container 100 containing the sample 120. The opening 110 can be sealed by a closure 130 attached to the laboratory sample container 100 by an adhesive 140. An adhesive strength AS1 of the adhesive 140 can be lowerable to an adhesive strength AS2 by treatment such as, for example from a first value AS1 to a second value AS2. The method can comprise a) treating the adhesive 140 such that its adhesive strength AS1 can be lowered an adhesive strength AS2 such as, for example, from the first value AS1 to the second value AS2 and b) removing the closure 130 from the laboratory sample container 100.

Furthermore, FIGS. 1 to 4 show a laboratory automation system 10 for handling the laboratory sample container 100 containing the sample 120. The laboratory automation system 10 can comprise a laboratory apparatus 20 for unsealing the opening 110 of the laboratory sample container 100 containing the sample 120. The opening 110 can be sealed by the closure 130 attached to the laboratory sample container 100 by the adhesive 140. The adhesive strength AS1 of the adhesive 140 can be lowerable to an adhesive strength AS2 by treatment. The laboratory apparatus 20 can comprise a treater 30 and a remover 40. The treater 30 can be configured to treat the adhesive 140 such that its adhesive strength AS1 can be lowered to an adhesive strength AS2. The remover 40 can be configured to remove the closure 130 from the laboratory sample container 100.

The laboratory automation system 10 can be configured to perform the method such as, for example, for handling the laboratory sample container 100, as described above. The laboratory apparatus 20 can be configured to perform the method such as, for example, for unsealing the opening 110 of the laboratory sample container 100, as described above.

Figure 4:
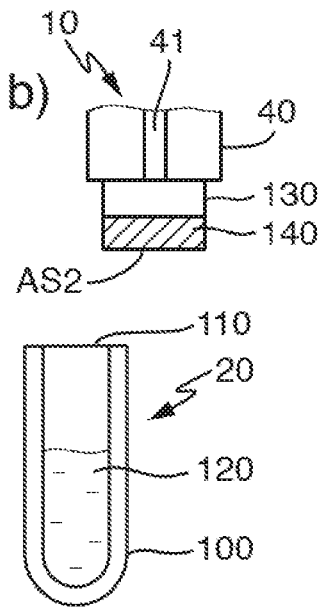
FIG. 4 illustrates schematically a method step for removing and a remover of the laboratory apparatus according to an embodiment of the present disclosure.

In detail, the laboratory sample container 100 can be designed as a tube. The upright laboratory sample container 100 can have the opening 110 at an upper end of a wall, as shown in FIG. 4. The laboratory sample container 100 can contain the sample 120 in the form of a liquid. The sample 120 does not have to completely fill the laboratory sample container 100. In other words, a surface of the sample 120 can be significantly away from the opening 110.

Figure 2:
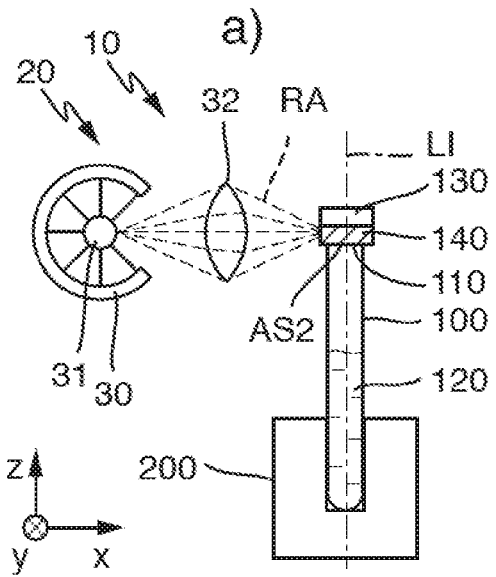
FIG. 2 illustrates schematically a method step for treating by radiation and a treater for treating by radiation of the laboratory apparatus according to an embodiment of the present disclosure.
Figure 3:
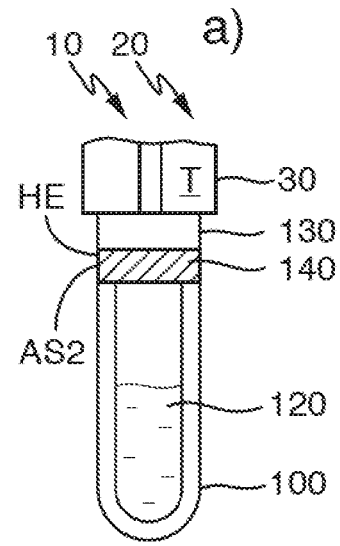
FIG. 3 illustrates schematically a method step for treating by heat according to the invention and a treater for treating by heat of the laboratory apparatus according to an embodiment of the present disclosure.

As shown in FIGS. 1 to 3, the opening 110 can be sealed by the closure 130. In the shown embodiment, the closure 130 can be embodied as a foil. In alternative embodiments, the closure may be embodied as a lid.

In the embodiment shown in FIGS. 1 and 2, the adhesive 140 can comprise a reactive site to UV radiation.

The adhesive strength AS1 of the adhesive 140 can be lowerable to an adhesive strength AS2 by radiation treatment such as, for example, by UV radiation RA.

The treater 30 can be configured to treat the adhesive 140 by radiation RA such as, for example, by UV radiation. In one embodiment, the treater 30 can comprise a radiation source 31 such as, for example, a UV radiation source 31.

Method step a) can comprise treating the adhesive 140 by radiation RA such as, for example, by UV radiation RA by the treater 30.

In detail, method step a) can comprise exposing the radiation RA to the adhesive 140 along a direction x different from such as, for example, substantially perpendicular to, a line LI between the adhesive 140 and the sample 120, as shown in FIG. 2. Additionally, method step a) can comprise focusing the radiation on the adhesive 140.

In one embodiment, the treater 30 can comprise an optic 32 such as, for example, for exposing the radiation RA to the adhesive 140 along the direction x different from the line LI between the adhesive 140 and the sample 120 and for focusing the radiation RA on the adhesive 140.

In alternative embodiments, method step a) may comprise either exposing the radiation to the adhesive along a direction different from a line between the adhesive and the sample or focusing the radiation on the adhesive. Additionally, or alternatively, in alternative embodiments, the treater may comprise an optic such as, for example, either for exposing the radiation to the adhesive along a direction different from a line between the adhesive and the sample or for focusing the radiation on the adhesive.

In the embodiment, shown in FIGS. 3 and 4, the adhesive 140 can comprise a foaming agent such as, for example, heat-expandable microspheres.

The adhesive strength AS1 of the adhesive 140 can be lowerable to an adhesive strength AS2 by heat treatment such as, for example, by heat HE with a temperature T with a minimum of about 50° C.

The treater 30 can be configured to treat the adhesive 140 by heat HE such as, for example, by heat with a temperature T with a minimum of about 50° C. In one embodiment, the treater 30 can comprise a heat source.

Method step a) can comprise treating the adhesive 140 by heat HE such as, for example, by heat HE with a temperature T with a minimum of about 50° C. such as, for example, by the treater 30.

In detail, the treater 30 can be brought, in heat or thermal contact with the adhesive 140 for the heat treating. In one embodiment, the treater 30 can be brought in direct contact with the closure 130, in FIG. 3, from the top and/or along the direction z. In alternative embodiments, the adhesive may be treated by thermal radiation such as, for example, by infrared radiation such as, for example, by a laser.

In the shown embodiments, the closure 130 can be left on the laboratory sample container 100 until after the treating of the adhesive 140 or the lowering of its adhesive strength to AS2, respectively. After the treating, the released closure 130 may be easily removed from the laboratory sample container 100.

In the embodiment shown in FIG. 1, the remover 40 can be configured to attach a take-up 42 to the closure 130 by another adhesive 43. Another adhesive strength AS3 of the another adhesive 43 can be such that another adhesive force between the take-up 42 and the attached closure 130 can be higher than an adhesive force between the closure 130 and the laboratory sample container 100 by the lowered adhesive strength AS2 of the treated adhesive 140. Furthermore, the remover 40 can be configured to remove the take-up 42 with the attached closure 130 from the laboratory sample container 100.

Method step b) can comprise attaching the take-up 42 to the closure 130 by the another adhesive 43 such as, for example, by the remover 40. The another adhesive strength AS3 of the another adhesive 43 can be such that the another adhesive force between the take-up 42 and the attached closure 130 can be higher than the adhesive force between the closure 130 and the laboratory sample container 100 by the lowered adhesive strength AS2 of the treated adhesive 140. Removing the take-up 42 with the attached closure 130 from the laboratory sample container 100 by the remover 40.

The take-up 42 such as, for example, a surface of the take-up 42, can be provided with the another adhesive 43.

In one embodiment, the another adhesive 43 can be pressure-sensitive and the take-up 42 can be attached to the closure 130 by pressing the take-up 42 against the closure 130, in FIG. 1 from the top and/or along the direction z as shown by arrows.

In detail, the remover 40 can comprise at least one roller receptacle and mover 60. The roller receptacle and mover 60 can be configured to supply the take-up 42 by a roller tape 160 such as, for example, of a take-up-roll 165. Furthermore, the roller receptacle and mover 60 can be configured to move the roller tape 160 with the take-up 42 with the attached closure 130 from the laboratory sample container 100, in FIG. 1 from the left to the right and/or along the direction x, z.

In one embodiment, the remover 40 can comprise a plurality of such as, for example, three, roller receptacles and movers 60. One roller receptacle and mover 60 can be configured to provide the take-up-roll 165 and to rotate the take-up-roll 165 and thereby the roller tape 160, as shown in FIG. 1 by arrows. This roller receptacle and mover 60 may be denoted as upstream-side roller. Another roller receptacle and mover 60 can be configured to provide a waste-roll 166 and to rotate the waste-roll 166 and thereby the roller tape 160. This roller receptacle and mover 60 may be denoted as downstream-side roller. Another roller receptacle and mover 60 can be configured to provide a release-liner-roll 167 and to rotate the release-liner-roll 167 and thereby a release liner roller tape 168.

The release liner roller tape 168 can be configured to protect the roller tape 160 and its take-up 42 and the another adhesive 43 before the unsealing and to be released from the roller tape 160 and its take-up 42 and the another adhesive 43 for the unsealing.

Furthermore, the release liner roller tape 168 can comprise or consist of polyester.

Moreover, the laboratory automation system 10 or its laboratory apparatus 20, respectively, can comprise a holder 200 such as, for example, in the form of a single holder for the single or only laboratory sample container 100. The holder 200 can be configured to hold the laboratory sample container 100 or its opening 110 aligned with respect to the treater 30 and/or the remover 40 for the unsealing such as, for example, in the upright position. In detail, the holder 200 can be configured to hold such as, for example, to surround, the laboratory sample container 100 at such as, for example, a lower part, of a circumference of the laboratory sample container 100.

In alternative embodiments, the laboratory automation system or its laboratory apparatus may comprise two holders, three holders or more than three holders or such as, for example, in one embodiment, at least ten holders or such as, for example, in another embodiment, or such as, for example, in yet another embodiment, at least one-hundred holders, or such as, for example, in still yet another embodiment, at least one-thousand holders. Additionally, or alternatively, in alternative embodiments, the laboratory automation system or its laboratory apparatus, respectively, may comprise at least one rack, or such as, for example, in one embodiment, for five laboratory sample containers, wherein the rack may be configured to hold the laboratory sample container(s) aligned with respect to treater and/or the remover for the unsealing.

Further, the laboratory automation system 10 or its laboratory apparatus 20 can comprise a movement unit 210. The movement unit 210 can be configured to move the laboratory sample container 100 or the holder 200 with the held laboratory sample container 100 to/from the treater 30 and/or the remover 40 such as, for example, with the opening 110 below the treater 30 and/or the remover 40, in FIG. 1 from the right to the left and/or along the direction x.

In the shown embodiment, the movement unit 210 can be embodied as a conveyor belt. In alternative embodiments, the movement unit may comprise or be a band and/or a laboratory sample container distribution system as described in EP 2 995 958 A1, which is hereby incorporated by reference.

In alternative embodiments, the laboratory automation system or its laboratory apparatus, respectively, may comprise either the holder or the movement unit.

In the embodiment shown in FIG. 4, the remover 40 can comprise a sucker 41. The sucker 41 can be configured to suck the closure 130 from the laboratory sample container 100 by vacuum.

Method step b) can comprise sucking the closure 130 from the laboratory sample container 100 by vacuum such as, for example, by the remover 40 or its sucker 41.

In one embodiment, the sucker 41 can comprise a vacuum chuck and/or a vacuum source.

The embodiment shown in FIGS. 3 and 4 may also comprise a holder and/or a movement unit as shown in the embodiment of FIGS. 1 and 2.

In the embodiment shown in FIGS. 3 and 4, the treater 30 such as, for example, in the form of the heat treater, and the remover 40 in the form of the sucker 41 can be embodied as one-piece or combined. In alternative embodiments, the treater and the remover may be embodied separate from each other.

In the embodiment, shown in FIG. 1, the treater 30 such as, for example, in the form of the radiation treater and the remover 40 such as, for example, with the roller tape 160, the take-up 42 and the adhesive 43 can be embodied as one-piece or combined. In detail, the roller tape 160, the take-up 42 and the adhesive 43 can be transparent for the radiation RA. In alternative embodiments, the treater and the remover may be embodied separate from each other.

Furthermore, in alternative embodiments, heat treating does not have to be combined with sucking by vacuum. In alternative embodiments, heat treating may be combined with attaching a take-up and removing the take-up. Additionally, or in the alternative, in alternative embodiments, radiation treating does not have to be combined with attaching a take-up and removing the take-up. In alternative embodiments, radiation treating may be combined with sucking by vacuum. In one embodiment, the sucker may be transparent for the radiation.

The above described treating method(s) can enable that less or no adhesive residues are left such as, for example, on the laboratory sample container 100, after the unsealing.

Furthermore, the above described removing method(s) can enable that less or no damage may be introduced to the laboratory sample container 100.

Thereby, a sealing such as, for example, a re-sealing, of the same opening 110 of the same laboratory sample container 100 can be facilitated.

Furthermore, the method for handling a laboratory sample container 100 containing a sample 120 can comprise the step sealing the opening 110 of the laboratory sample container 100 such as, for example, before the unsealing. The sealing can comprise attaching a closure 130 to the laboratory sample container 100 by an adhesive 140, as shown in FIGS. 5 to 8. An adhesive strength AS1 of the adhesive 140 can be lowerable to an adhesive strength AS2 by treatment such as, for example, from a first value AS1 to a second value AS2.

Moreover, the laboratory automation system 10 for handling the laboratory sample container 100 containing the sample 120 can comprise a sealer 70, as shown in FIGS. 5 to 8. The sealer 70 can be configured to seal the opening 110 of the laboratory sample container 100 by attaching the closure 130 to the laboratory sample container 100 by the adhesive 140. The adhesive strength AS1 of the adhesive 140 can be lowerable to an adhesive strength AS2 by treatment.

The laboratory automation system 10 or its sealer 70 can be configured to perform the method such as, for example, sealing the opening 110 of the laboratory sample container 100, as described above.

The closure 130 such as, for example, a surface of the closure 130, can be provided with the adhesive 140.

In detail, the adhesive 140 can be pressure-sensitive.

Figure 5:
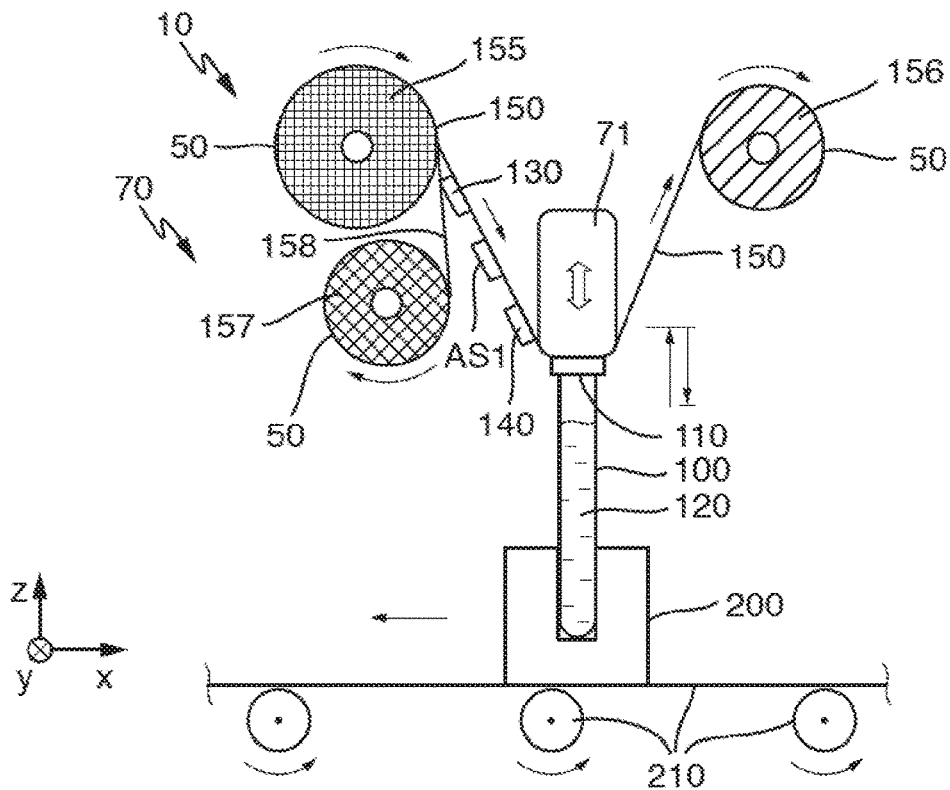
FIG. 5 illustrates schematically a method step for sealing the opening of the laboratory sample container and a sealer for sealing the opening of the laboratory sample container of the laboratory automation system according to an embodiment of the present disclosure.
Figure 7:
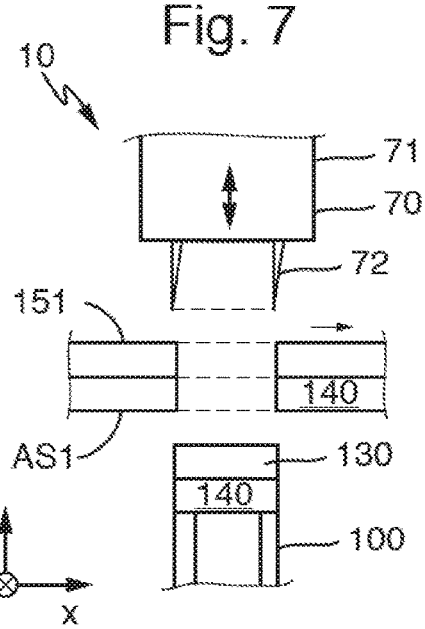
FIG. 7 illustrates schematically a method step for sealing the opening of the laboratory sample container comprising method steps for attaching a closure blank to the laboratory sample container and cutting-out a closure out of the closure blank and a sealer for sealing the opening of the laboratory sample container by attaching the closure blank to the laboratory sample container and cutting-out the closure out of the closure blank of the laboratory automation system according to an embodiment of the present disclosure.

The sealer 70 can be configured to press the closure 130 against the laboratory sample container 100, in FIGS. 5 and 7, from the top and/or along the direction z as shown by arrows. In one embodiment, the sealer 70 can comprise a pressure pad 71.

The sealing can comprise pressing the closure 130 against the laboratory sample container 100 such as, for example, with the adhesive 140 in between the closure 130 and the laboratory sample container 100 such as, for example, by the sealer 70 or its pressure pad 71.

The sealer 70 can comprise at least one roller receptacle and mover 50. The roller receptacle and mover 50 can be configured to supply the closure 130 by a roller tape 150, 151 such as, for example, of a closure-supply-roll 155 or a closure-blank-supply-roll. Furthermore, the roller receptacle and mover 50 can be configured to move the roller tape 150, 151 with the closure 130 to the opening 110 of the laboratory sample container 100 for the sealing, in FIGS. 5 and 7, from the left to the right and/or along the direction x, z.

The method can comprise the steps of supplying the closure 130 by the roller tape 150, 151 such as, for example, by the at least one roller receptacle and mover 50 and moving the roller tape 150, 151 with the closure 130 to the opening 110 of the laboratory sample container 100 for the sealing such as, for example, by the at least one roller receptacle and mover 50.

In one embodiment, the sealer 70 can comprise a plurality of such as, for example, three, roller receptacles and movers 50. One roller receptacle and mover 50 can be configured to provide the closure-supply-roll 155 and/or the closure-blank-supply-roll and to rotate the closure-supply-roll 155 and/or the closure-blank-supply-roll and thereby the roller tape 150, 151, as shown in FIGS. 5 and 7 by arrows. This roller receptacle and mover 50 may be denoted as upstream-side roller. Another roller receptacle and mover 50 can be configured to provide a carrier-roll and/or a waste-roll 156 and to rotate the carrier-roll and/or the waste-roll 156 and thereby the roller tape 150, 151. This roller receptacle and mover 50 may be denoted as downstream-side roller. Another roller receptacle and mover 50 can be configured to provide a release-liner-roll 157 and to rotate the release-liner-roll 157 and thereby a release liner roller tape 158.

The release liner roller tape 158 can be configured to protect the roller tape 150, 151 and its closure 130 before the sealing and to be released from the roller tape 150,151 and its closure 130 for the sealing.

Furthermore, the release liner roller tape 158 can comprise or consist of polyester.

Moreover, the laboratory automation system 10 or its sealer 70 can comprise a holder 200 such as, for example, in the form of a single holder for the single or only laboratory sample container 100. The holder 200 can be configured to hold the laboratory sample container 100 or its opening 110 aligned with respect to the sealer 70 for the sealing such as, for example, in the upright position.

In detail, the holder 200 is or may be embodied as the holder 200 described above for the embodiment shown in FIG. 1.

Additionally, or alternatively, in alternative embodiments, the laboratory automation system or its sealer, respectively, may comprise at least one rack such as, for example, for five laboratory sample containers, wherein the rack may be configured to hold the laboratory sample container(s) aligned with respect to the sealer for the sealing.

Further, the laboratory automation system 10 or its sealer 70 can comprise a movement unit 210. The movement unit 210 can be configured to move the laboratory sample container 100 or the holder 200 with the held laboratory sample container 100 to/from the sealer 70 such as, for example, with the opening 110 below the sealer, in FIGS. 5 and 7 from the right to the left and/or along the direction x.

In detail the movement unit 210 is or may be embodied as the movement unit 210 described above for the embodiment shown in FIG. 1.

In alternative embodiments, the laboratory automation system or its sealer may comprise either the holder or the movement unit.

Figure 6:
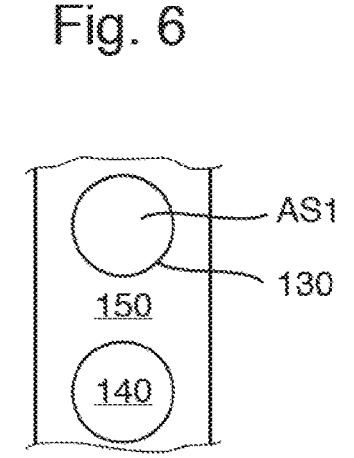
FIG. 6 illustrates schematically a roller tape with a closure according to an embodiment of the present disclosure.

In the embodiment shown in FIGS. 5 and 6, the closure 130 can be pre-cut and available from the roller tape 150 such as, for example, of the closure-supply-roll 155.

Figure 8:
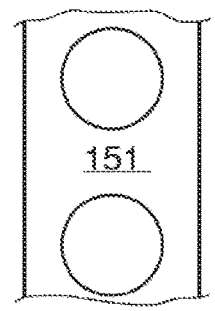
FIG. 8 illustrates schematically a roller tape of FIG. 7 from which the closure of FIG. 7 is cut-out according to an embodiment of the present disclosure.

In the embodiment shown in FIGS. 7 and 8, the sealer 70 can be configured to attach a closure blank 151 such as, for example, the roller tape 151, to the laboratory sample container 100, in FIG. 7, from the top and/or along the direction z as shown by an arrow. Furthermore, the sealer 70 can be configured to cut-out the closure 130 out of the attached closure blank 151 such as, for example, the roller tape 151.

In one embodiment, the sealer 70 can comprise an attacher 71 such as, for example, in the form of the pressure pad 71, and a cutter 72 such as, for example, in the form of a blade 72. In the embodiment shown in FIGS. 7 and 8, the attacher 71 and the cutter 72 can be embodied as one-piece or combined. In alternative embodiments, the attacher and the cutter may be embodied separate from each other.

The sealing can comprise attaching the closure blank 151 such as, for example, the roller tape 151, to the laboratory sample container 100 such as, for example, by the sealer 70 or its attacher 71. Cutting-out the closure 130 out of the closure blank 151 such as, for example, the roller tape 151 such as, for example, by the sealer 70 or its cutter 72.

The closure blank 151 such as, for example, a surface of the closure blank 151, can be provided with the adhesive 140.

In detail, the closure blank 151 may be supplied by the roller tape 151 such as, for example, as described above for the embodiment shown in FIG. 5.

In one embodiment, a part of the roller tape 151, which covers the opening 110 of the laboratory sample container 100, can be cut-out from the roller tape 151 by the cutter 72 in the form of the cylindrical blade. After the cutting-out, the roller tape 151 can still be connected, as shown in FIG. 8, such as, for example, in between the closure-blank-supply-roll and the waste-roll.

The laboratory apparatus 20 or its treater 30 and/or its remover 40 and/or the laboratory automation system 10 or its sealer 70 may be denoted as a laboratory station(s). Beyond that, the laboratory automation system may comprise a number of other laboratory stations. The movement unit 210 is or may be configured to move the laboratory sample container 100 between the laboratory stations.

As the above discussed embodiments reveal, a method for unsealing an opening of a laboratory sample container in an improved manner than in the prior arts such as, for example, in a soft manner is disclosed. Furthermore, a method for handling a laboratory sample container comprising such a method, a laboratory apparatus for unsealing an opening of a laboratory sample container and a laboratory automation system comprising such a laboratory apparatus is also disclosed.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory apparatus for unsealing an opening of a laboratory sample container containing a liquid sample, wherein the opening is sealed by a closure attached to the laboratory sample container by an adhesive, wherein an adhesive strength of the adhesive is lowerable by treatment, the laboratory apparatus comprising:
    a UV radiation treater that during operation causes the a material of the adhesive to undergo an adhesive strength reduction through crosslinking, the UV radiation treater configured to impart radiation to the adhesive along a direction that is substantially perpendicular to a line between the adhesive and the liquid sample;
    a remover comprising at least one roller receptacle and mover; and
    a movement unit configured to convey the sample container containing the liquid sample to keep the opening in an upright position, as well as to place the sample container in contact with the remover such that during operation the remover attaches a take-up to the closure by another adhesive that has an adhesive strength such that an adhesive force between the take-up and the attached closure is higher than an adhesive force between the closure and the laboratory sample container such that the take-up with the attached closure is removed from the laboratory sample container while keeping the sample container in the upright position, wherein the at least one roller receptacle and mover are configured to supply the take-up by a roller tape and to move the roller tape with the take-up with the attached closure from the laboratory sample container.

2. The laboratory apparatus according to claim 1, wherein the remover further comprises a sucker cooperative with the closure to effect a vacuum-based removal of the closure from the laboratory sample container.

3. A laboratory automation system for handling the laboratory sample container containing the liquid sample, the laboratory automation system comprising:
    a sealer, wherein the sealer is configured to seal the opening of the laboratory sample container by attaching the closure to the laboratory sample container by the adhesive, wherein the adhesive strength of the adhesive is lowerable by treatment; and
    a laboratory apparatus according to claim 1.

4. The laboratory automation system according to claim 3, wherein the sealer comprises at least one roller receptacle and mover, wherein the roller receptacle and mover of the sealer is configured to supply the closure by a roller tape of the sealer and to move the roller tape of the sealer with the closure to the opening of the laboratory sample container for the sealing.

5. The laboratory apparatus according to claim 1, wherein the UV radiation treater further comprises a heat source.

6. The laboratory apparatus according to claim 1, further comprising a holder placed on the movement unit to convey the laboratory sample container into selective cooperation with at least one of the treater and remover.

7. The laboratory apparatus according to claim 6, wherein the holder is configured to circumferentially contain at least a lower portion of the laboratory sample container.

8. The laboratory apparatus according to claim 1, wherein the UV radiation treater is angled to impart the radiation to the adhesive while not to the liquid sample.

* * * * *